United States Patent

Loev et al.

[11] Patent Number: 4,534,979
[45] Date of Patent: Aug. 13, 1985

[54] POLYENE COMPOUNDS USEFUL IN THE TREATMENT OF PSORIASIS AND ALLERGIC RESPONSES

[75] Inventors: Bernard Loev, Scarsdale; Wan-Kit Chan, Yorktown Heights, both of N.Y.; Howard Jones, Holmdel, N.J.

[73] Assignee: USV Pharmaceutical Corp., Tarrytown, N.Y.

[21] Appl. No.: 667,703

[22] Filed: Nov. 2, 1984

Related U.S. Application Data

[63] Continuation-in-part of Ser. No. 511,822, Jul. 8, 1983, which is a continuation-in-part of Ser. No. 392,837, Jun. 28, 1982, Pat. No. 4,472,430.

[51] Int. Cl.$^3$ .................... A61K 31/18; A61K 31/19; A61K 31/23
[52] U.S. Cl. .................................. 514/529; 514/543; 514/545; 514/557; 514/570; 514/613; 514/621; 514/622; 514/617; 514/532
[58] Field of Search .......................................... 424/312

[56] References Cited
PUBLICATIONS
Chem. Abst. 62-2798g (1965).

Primary Examiner—Stanley J. Friedman

[57] ABSTRACT

Polyene compounds represented by the general formulae

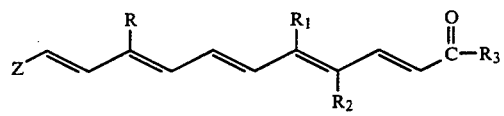

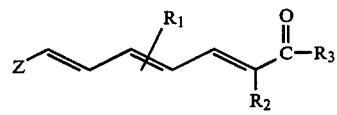

in which:
R and $R_1$ are each hydrogen or an alkyl group of from 1 to 5 carbon atoms;
$R_2$ is an alkyl group of from 1 to 5 carbon atoms;
$R_3$ is hydroxyl, alkoxy of from 1 to 5 carbon atoms, $NH_2$, $NHR_2$ or $NR_2R_2$ and Z is a cycloalkyl, cycloalkenyl or cycloalkdienyl group substituted with from 0 to 5 alkyl groups, a keto group or a hydroxyl group or a phenyl group substituted with from 0 to 4 hydroxy, alkoxy, alkyl, aryloxy, aralkyloxy or trifluoromethyl groups or halogen atoms or combinations thereof and the pharmaceutically-acceptable salts thereof.

The foregoing compounds have been found to be effective in the treatment of psoriasis, inflammatory conditions and allergic responses.

2 Claims, No Drawings

POLYENE COMPOUNDS USEFUL IN THE TREATMENT OF PSORIASIS AND ALLERGIC RESPONSES

This is a continuation-in-part application of application Ser. No. 511,822, filed July 8, 1983 which in turn is a continuation-in-part application of application Ser. No. 392,837, filed June 28, 1982, now U.S. Pat. No. 4,472,430.

BACKGROUND OF THE INVENTION

The present invention relates to polyene compounds and more particularly to novel alpha-alkyl polyolefinic carboxylic acids derived from such polyolefinic intermediates as retinal (3,7-dimethyl-9-(2,6,6-trimethyl-1-cyclohexen-1-yl)-2,4,6,8-nonatetraenal; vitamin A aldehyde) which possesses the structure

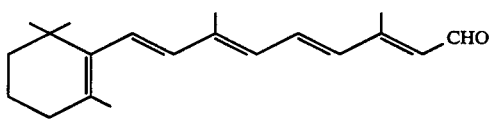

A synthesis of retinal from beta-ionone and propargyl halide is described in U.S. Pat. No. 3,060,229.

A number of alpha-substituted polyolefinic carboxylic aldehydes, acids and esters are described in the scientific literature. Japanese Pat. No. 10,124 (1964); C.A. 62, 2798 g (1965) describes 2,7-dimethyl-9-(2,6,6-trimethyl-1-cyclohexen-1-yl)-2,4,6,8-nonatetraenonic acid and 2,7,11-trimethyl-13-(2,6,6-trimethyl-1-cyclohexen-1-yl)-2,4,6,8,10,12-tridecahexanenoic acid; Machleidt, et al., *Justus Liebigs Ann. Chem.*, 679,20 (1964) describes α-fluoropolyolefinic acids and esters; Chan, et al., *J.A.C.S.* 96, 3642 (1974) describe polyolefinic carboxaldehydes; Haeck, et al., *Recuil* 85 (1966) pp 334–338 describe 5,9-dimethyl-11-(2,6,6-trimethyl-1-cyclohexen-1-yl)-2,4,6,8,10-undecapentaenoic acid and corresponding 2,4,6,8,10,12-tridecahexanenoic acids as well as the corresponding α-cyano and α-carboxy substituted compounds. Buchta, et al., *Naturwissenschaften* 46, 74 (1959) describe methyl-2-methyl-7-phenyl)-2,4,6-heptatrienoate.

SUMMARY OF THE INVENTION

The present invention is directed to polyene compounds of the general formulae

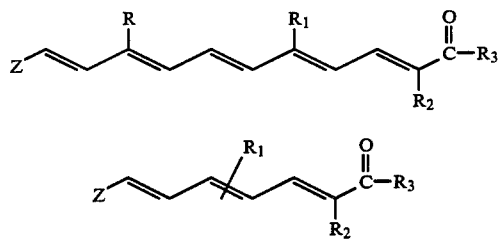

in which:
R and $R_1$ are each hydrogen or an alkyl group of from 1 to 5 carbon atoms;
$R_2$ is an alkyl group of from 1 to 5 carbon atoms;
$R_3$ is hydroxyl, alkoxy of from 1 to 5 carbon atoms, $NH_2$, $NHR_2$ or $NR_2R_2$ and Z is a cycloalkyl, cycloalkenyl or cycloalkdienyl group substituted with from 0 to 5 alkyl groups, a keto group or a hydroxyl group, or a phenyl group substituted with from 0 to 4 hydroxy, alkoxy, alkyl or trifluoromethyl groups or halogen atoms or combinations thereof; and the pharmaceutically-acceptable salts thereof. The invention includes compounds wherein the double bonds are in the cis or trans configuration.

The foregoing compounds have been found to be effective in the treatment of psoriasis, acne, and cellular and humoral immunodeficiancy.

Compounds of the foregoing invention have also been found active in regulating the formation of lipoxygenase and as such possess therapeutic value in the treatment of inflammatory conditions and allergic responses.

DESCRIPTION OF THE PREFERRED EMBODIMENTS

A preferred group of compounds within the aforesaid general formula are those in which $R_1$ is methyl, $R_3$ is hydroxyl or alkoxy of from 1 to 5 carbon atoms and Z is a cycloalkenyl group substituted with from 0 to 3 alkyl groups, or a phenyl group substituted with from 1 to 4 alkoxy or alkyl groups containing up to 5 carbon atoms or combinations of the foregoing, including those compounds in which one or more of the double bonds are in the cis configuration. Within this preferred group of compounds, still more preferred are compounds in which Z is the group 2,6,6-trimethyl-1-cyclohexen-1-yl.

The compounds of this invention can be prepared from known polyolefinic materials, e.g., retinal, employing known synthetic procedures of from analogous polyolefinic compounds which can be prepared in accordance with methods known by those skilled in the art.

For example, employing retinal as starting compound, condensation through the aldehyde group with the active methylene group of suitable acids or acid derivatives of the formula:

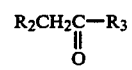

will result in the corresponding undecapentaenoic acid derivative. Activating substituents on the alpha carbon atom of the said compounds, e.g., trialkylphosphono derivatives, facilitate the condensation reaction.

The condensation reaction is usually carried out by reacting the selected starting materials in a suitable solvent preferably in the presence of a strong base such as sodium hydride, sodamide, sodium ethoxide and similar alkali metal compounds. The reaction is usually exothermic and is consequently cooled to control the rate of reaction. After the initial reaction has subsided, the reaction mixture is heated at refulx to assure completeness of reaction.

A variety of reaction solvents can be employed including dioxane, tetrahydrofuran (THF), dimethylformamide, dimethylacetamide and similar water-miscible organic solvents. The solvents employed are preferably anhydrous, particularly when the alkali metal bases are used, to avoid secondary reactions.

The present new compounds can also be prepared from corresponding compounds containing only alpha hydrogen by alkylation using alkylating agents such as dialkyl sulfates, e.g., dimethyl and diethyl sulfate and alkyl halides, e.g., propyl bromide and ethyl bromide, in the presence of alkali metals or alkali metal compounds which react with alpha halogen, e.g., sodium hydride, lithium, potassium, sodamide and alkali metal alkoxides such as sodium or potassium ethoxide.

The compounds of this invention are also prepared by partial reduction of corresponding compounds containing acetylenic in lieu of ethylenic bonds. In addition, the dehydrohalogenation of corresponding alpha-halo acid with no ethylenic bond between alpha and beta carbon atoms also leads to the present compounds.

A further preparative method involves condensation of appropriate side chains with the appropriate side chains with the appropriately substituted cyclohexanone with, for example, an omegahaloundecapentaenoate, preferably in the form of the corresponding Grignard reagent, followed by hydrolysis of the product to form the α-substituted cyclohexanol and then dehydration to the cyclohexenyl compound. The side chain, i.e., the eleven carbon side chain can be formed piecemeal by suitable condensation employing the half aldehyde of a dicarboxylic acid of suitable carbon content to condense with a side chain of suitable carbon content with groups suitable to react with the aldehyde functional group.

A still further process can be used involving oxidation of derivatives of the desired undecapentaenoic acid with mild oxidants such as hypochlorite, e.g., sodium hypochlorite. The oxidants selected should preferably avoid secondary reactions with the remainder of the substrate molecule, or the oxidation should be carried out under controlled conditions to avoid appreciable secondary reactions, as by conducting oxidation with hypochlorite solution at or below about 10° C. and preferably between 0° and 5° C. For example, a compound of the formula

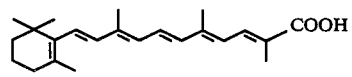

on oxidation with hypochlorite yields the corresponding acid of formula I herein. These new compounds can also be prepared by dehydration of corresponding α or β hydroxy acids or esters to form an alpha-beta ethylenic bond. The beta hydroxy acids or esters can be formed by condensation of an alpha-halocarboxylic acid (or ester) with an aldehyde of two carbons less than the desired side chain in the presence of zinc (the Reformatsky Reaction).

The present compounds can also be prepared by oxidation of the corresponding aldehyde and alcohol of the same carbon content using oxidizing agents known for such reaction, e.g., hypochlorite, as previously described.

EXAMPLE 1

Ethyl 2,5,9-Trimethyl-11-(2,6,6-trimethyl-1-cyclohexen-1-yl)-2,4,6,8,10,-undecapentaenoate

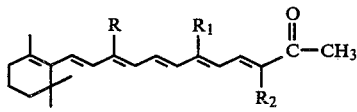

Sodium hydride (4.03 g, 50%) dispersion in mineral oil was washed with dry pentane three times and suspended in 50 ml of anhydrous THF under nitrogen. The stirred mixture was cooled in an ice-water bath and 20.6 g of triethyl 2-phosphonopropionate was added dropwise. The resulting mixture was stirred for additional two hours while allowing the reaction mixture to warm up slowly to room temperature. The mixture was then cooled in an ice-water bath and a solution of retinal (16 g) in 50 ml of anhydrous THF was added dropwise. The resulting dark red mixture was stirred for four hours at room temperature; 700 ml of cold water was added and the mixture was extracted with three 200-ml portions of ether. The combined ethereal solution was washed with 100 ml of water and dried over sodium sulfate. Removal of solvent gave the crude ester (20 g, 97%) as a dark red oily substance. This material was used for the preparation of the free acid of Example 2 without further purification.

EXAMPLE 2

2,5,9-Trimethyl-11-(2,6,6-trimethyl-1-cyclohexen-1-yl)-2,4,6,8,10-Undecapentaenoic Acid

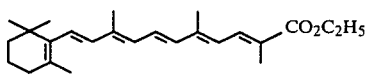

The crude ethyl ester (20 g) from Example 1 was dissolved in 50 ml of ethanol and a solution of potassium hydroxide (5.12 g) in 45 ml of ethanol and 5 ml of water was added dropwise with stirring under nitrogen. The resulting mixture was stirred for 12 hours at room temperature. The reaction mixture was partially concentrated under reduced pressure and then mixed with 500 ml of water. The resulting mixture was extracted with three 150 ml portions of ether. The ethereal layer was discarded, the aqueous layer was acidified to pH 3 with 10N aqueous hydrochloric acid. The resulting product was extracted into ether. The etheral solution was washed with water and dried over sodium sulfate. Concentration and filtration of this solution afforded the desired product as orange-red powders. Recrystallization in acetone/ethanol gave 9.3 g (50.6%) of pure product, mp 197°–199° C., UV spectrum (methanol) max 380 nm.

EXAMPLE 3A

Triethyl 2-Phosphonobutyrate

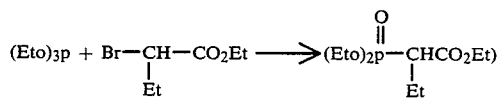

A mixture of ethyl 2-bromobutyrate (100 g, 0.5/mole and triethyl phosphite (85.2 g, 0.5/mole) was heated in an oil bath at 145° C. for 2 hrs. After cooling to room temperature, the reaction mixture was distilled at atmospheric pressure to remove the bulk of the ethyl bromide. The desired product was then distilled at 80°–95° C. (0.15 mm of Hg). Obtained: 60 g of triethyl 2-phosphonobutyrate as colorless clear liquid.

EXAMPLE 3B 5,9-Dimethyl-2-Ethyl-11-(2,6,6-Trimethyl-1-Cyclohexen-1-yl)-2,4,6,8,10-Undecapentaenoic Acid

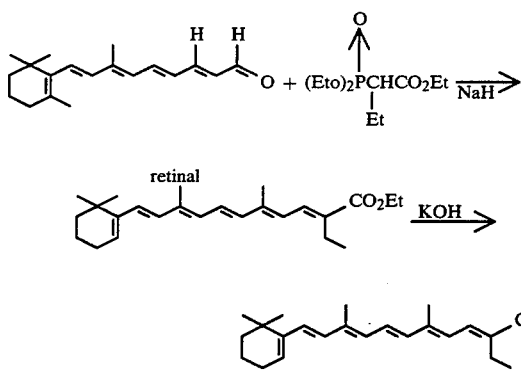

In analogy to the procedure given in Example 1: Triethyl 2-phosphonobutyrate was reacted with retinal to give ethyl 5,9-dimethyl-2-ethyl-11-(2,6,6-trimethyl-1cyclohexen-1-yl)-2,4,6,8,10-undecapentaenoate, which was converted by the procedure of Example 2 to 5,9-dimethyl-2-ethyl-11-(2,6,6-trimethyl-1-cyclohexen-1-yl)-2,4,6,8,10-undecapentaenoic acid, m.p.=164°–165° C.

EXAMPLE 4A

Triethyl 2-Phosphonovalerate

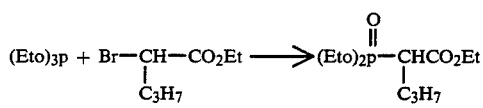

In analogy to the procedure given in Example 3: Ethyl 2-bromovalerate was treated with triethylphosphite to give triethyl 2-phosphonovalerate as a colorless clear liquid, b.p.=95°–110° C. (0.175 mm of Hg).

EXAMPLE 4B 5,9-Dimethyl-11-(2,6,6-Cyclohexen-1-yl)-2-Propyl-2,4,6,8,10-Undecapentaenoic Acid

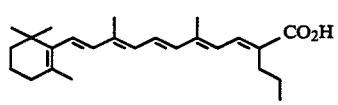

In analogy to the procedure described in Example 1: Triethyl 2-phosphonovalerate was reacted with retinal to give ethyl 5,9-dimethyl-11-(2,6,8-cyclohexen-1-yl)-2-propyl-2,4,6,8,10-undecapentaenoate, which was converted by the procedure of Example 2 to 5,9-dimethyl-11-(2,6,6-cyclohexen-1-yl)-2-propyl-2,4,6,8,10-undecapentaenoic acid, m.p.: 172°–175° C.

EXAMPLE 5

Methyl 7-(4-Benzyloxyphenly)-5-Methyl-Hepta-2,4,6-Trienoate

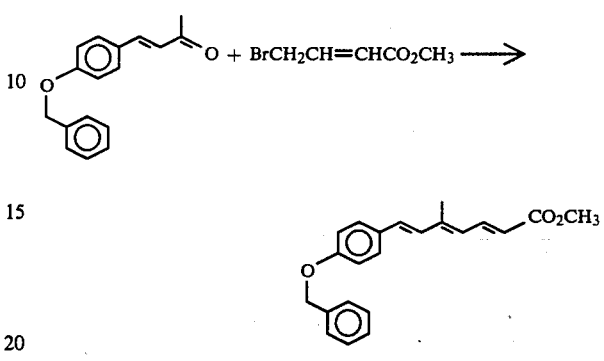

In a 2-l, three-necked, round bottomed flask, equipped with a reflux condenser and a mechanical stirrer, was placed 37.8 g (0.15M) of 4-(4-benzyloxyphenyl)-3-buten-2-one, 26 ml (85% reagent, 0.18M) of methyl 4-bromocrotonate, 13.2 g of activated zinc dust and 400 ml of anhydrous toluene. The mixture was warmed up slowly with stirring until a vigorous exothermic reaction occurred. At this moment, the heating was disconnected in order to prevent the reaction mixture from overflowing. After the exothermic reaction had subsided, the content was refluxed gently for one hour. After cooling down to room temperature, the reaction mixture was treated with 100 ml of 2N acetic acid and the mixture was stirred for 20 min. The layers were separated, the organic layer was washed with water, saturated sodium bicarbonate and water again, dried (magnesium sulfate), and concentrated on rotary evaporator to give a dark red oily residue. This substance was purified by dry column chromatography (silica gel, 20% ethyl acetate in hexane) to give 17.5 g of the product as a deep orange-colored oil. MS(EI): 334(m+).

EXAMPLE 6

7-(4-Benzyloxyphenyl)-5-Methyl-Hepta-2,4,6-Trienoic Acid

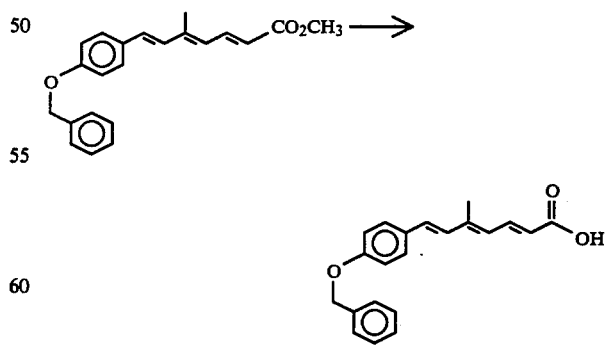

A mixture of methyl 7-(4-benzyloxyphenyl)-5-methyl-hepta-2,4,6-trienoate (3.2 g, 9.7 mmol) and potassium hydroxide (1.1 g, 19.4 mmol) in 200 ml of ethanol and 10 ml of water was stirred under nitrogen at room temperature for 48 hrs. The mixture was then concentrated on rotary evaporator and water (250 ml) was added. The solution was extracted with 30 ml of ethyl acetate; the aqueous layer was acidified with 10N HCl to pH 3. The yellow precipitate formed was extracted into ethyl acetate, washed with 30 ml of water, dried (magnesium sulfate) and concentrated on rotary evaporator to give a yellow powder, which was triturated with ethyl acetate to give 1.7 g of the product as yellow powder, mp: 210° C. (sublimed).

EXAMPLE 7

Methyl 7-(4-Methoxy-2,3,6-trimethylphenyl)-5-Methyl-Hepta-2,4,6-Trienoate

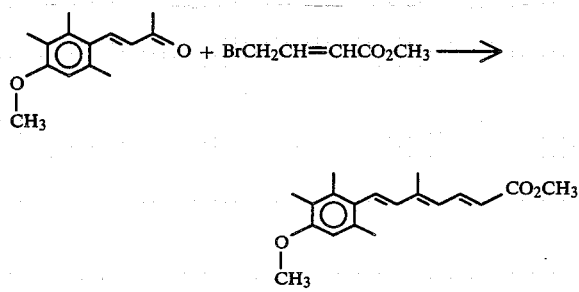

In a manner similar to Example 5, reaction of 4-(4-methoxy-2,3,6-trimethylphenyl)-3-buten-2-one with methyl 4-bromocrotonate afforded the desired compound. Crystallization from ether-petroleum ether gave yellow crystals, m.p. 104°–109° C. MS(EI): 300(m+), 285(m+—CH$_3$), 241(m+—CO$_2$CH$_3$).

EXAMPLE 8

7-(4-Methoxy-2,3,6-Trimethylphenyl)-5-Methyl-Hepta-2,4,6-Trienoic Acid

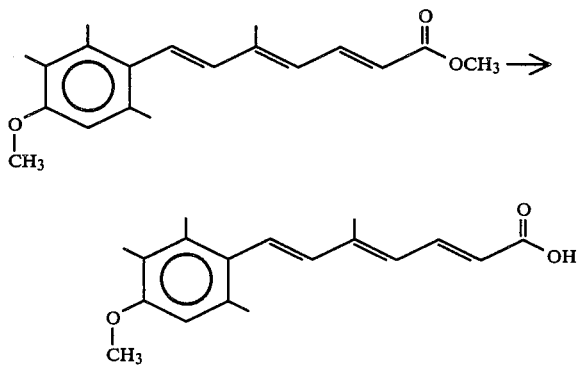

In a manner similar to Example 6, hydrolysis of methyl 7-(4-methoxy-2,3,6-trimethylphenyl)-5-methyl-hepta-2,4,6-trienote afforded the acid as yellow powder. Crystallization from acetone gave yellow crystals, m.p. 189°–191° C.; UV(MeOH): max 320 nm.

EXAMPLE 9

Methyl 7-(4-Hexyloxyphenyl)-5-Methyl-Hepta-2,4,6-Trienoate

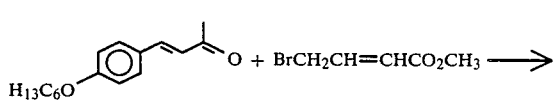

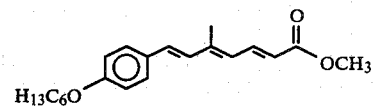

In a manner similar to Example 5, treatment of 4-(4-hexyloxyphenyl)-3-buten-2-one with methyl 4-bromocrotonate gave the title compound as an orange-colored oil. MS(EI): 314(m+).

EXAMPLE 10

7-(4-Hexyloxyphenyl)-5-Methyl-Hepta-2,4,6-Trienoic Acid

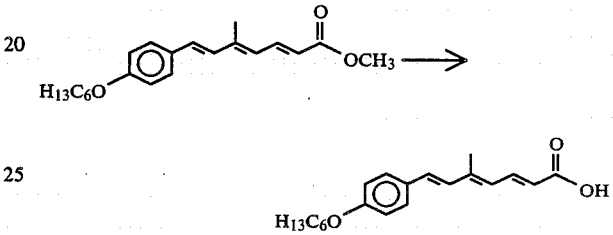

In a manner similar to Example 6, alkaline hydrolysis of methyl 7-(4-hexyloxyphenyl)-5-methyl-hepta-2,4,6-trienoate afforded, after trituration from ethyl acetate, the acid as yellow powder, m.p. 181°–185° C.

EXAMPLE 11

Ethyl 7-(4-Methoxy-2,3,6-Trimethylphenyl)-2-Methyl-Hepta-2,4,6-Trienoate

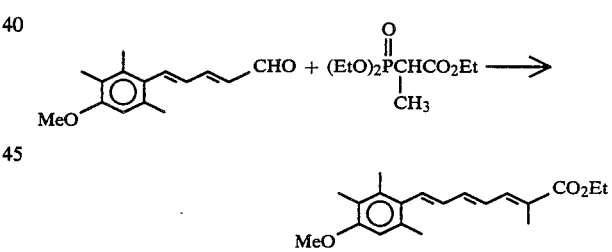

To a suspension of NaH (2g of 50% reagent) in 100 ml of tetrahydrofuran (THF), stirred under an atmosphere of nitrogen at 0° C., (ice bath), was added dropwise 8.8 g (37 mmol) of triethyl 2-phosphonopropionate. The resulting mixture was stirred in the ice bath for additional 2.5 hrs and a solution of 5-(4-methoxy-2,3,6-trimethylphenyl)-penta-2,4-dien-1-al (8.4 g, 37 mmol) in 20 ml of THF was added. The mixture was stirred at room temperature for 4 hrs.

The reaction mixture was quenched with 75 ml of brine and extracted with ethyl acetate several times. The combined organic layer was washed with brine, dried (magnesium sulfate) and concentrated on rotary evaporator to give 8.8 g of yellow oil. Purification by a silica gel dry column (20% ethyl acetate in hexane) yielded 6.3 g of pure material as a yellow oil. MS(EI): 314 (m+).

EXAMPLE 12

7-(4-Methoxy-2,3,6-Trimethylphenyl)-2-Methyl-Hepta-2,4,6-Trienoic Acid

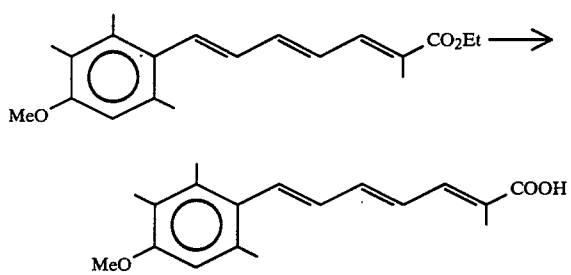

In a manner similar to Example 6, alkaline hydrolysis of ethyl 7-(4-methoxy-2,3,6-trimethylphenyl)-2-methyl-hepta-2,4,6-trienoate gave the acid as yellow powder, m.p. 179°–180° C.

EXAMPLE 13

5-(2,5-Dimethyl-4-Methoxyphenyl)-3-Methyl-Penta-2,4-Dien-1-al

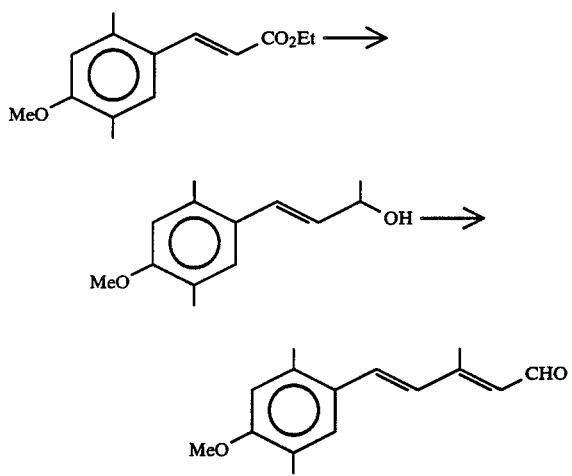

To 0.3M of methyl magnesium iodide in 100 ml of ether, stirred under a nitrogen atmosphere and in a cooling bath of −5° C., was added dropwise a solution of ethyl 3-(2,5-dimethyl-4-methoxyphenyl)-acrylate (23.4 g, 0.1M) in 50 ml of diethyl ether. This mixture was stirred for 3 hours at room temperature. Cold water (150 ml) was added, and the product was extracted into ether. The ethereal layer was washed with brine, dried (magnesium sulfate) and concentrated on rotary evaporator to give 21.4 g of 4-(2,5-dimethyl-4-methoxyphenyl)-2-methyl-3-buten-2-ol as yellow powder.

4-(2,5-dimethyl-4-methoxyphenyl)-2-methyl-3-buten-2-ol (18 g, 0.08M) in 25 ml of N,N-dimethylformamide (DMF) was added dropwise at 0° C. (ice bath) to the Vilsmeier reagent prepared from 15.4 g of phosphorus oxychloride and 15 ml of DMF. The resulting mixture was heated slowly to 80° C. and was stirred at this temperature for 4 hrs. The content of reaction flask was poured into 250 ml of ice-water mixture and sodium acetate (80 g) was added slowly in portions. The product was then extracted into ether. After work-up, the residue was purified by a silica gel dry column (15% ethyl acetate in hexane) to give 12 g of pure material as yellow powder, m.p. 90°–92° C. MS(CI): 231(m++1).

EXAMPLE 14

Ethyl 2,5-Dimethyl-7-(2,5-Dimethyl-4-Methoxyphenyl)-Hepta-2,4,6-Trienoate

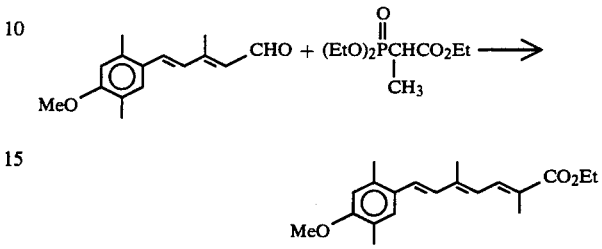

In a manner similar to Example 11, Wittig-Horner reaction between 5-(2,5-dimethyl-4-methoxyphenyl)-3-methyl-penta-2,4-dien-1-al and triethyl phosphonopropionate, followed by dry column chromatography (silica gel, 15% ethyl acetate in hexane) of the crude reaction product, gave the pure ester as a yellow oil. MS(EI): 314(m+).

EXAMPLE 15

2,5-Dimethyl-7-(2,5-Dimethyl-4-Methoxyphenyl)-Hepta-2,4,6-Trienoic Acid

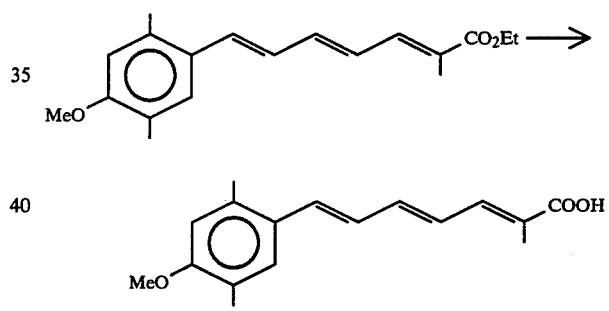

In a manner similar to Example 6, alkaline hydrolysis of ethyl 2,5-dimethyl-7-(2,5-dimethyl-4-methoxyphenyl)-hepta-2,4,6-trienoate gave the acid as yellow powder, m.p. 222°–224° C.

EXAMPLE 16

Ethyl-2,5-Dimethyl-7-(4-Methoxy-2,3,6-Trimethylphenyl)-Hepta-2,4,6-Trienoate

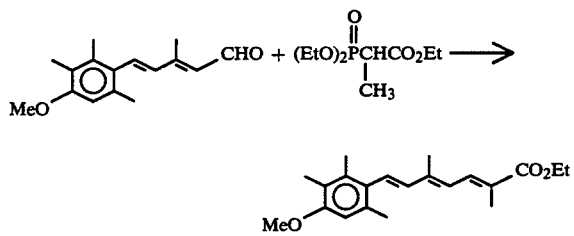

In a manner similar to Example 11, treatment of 5-(4-methoxy-2,3,6-trimethylphenyl)-3-methyl-penta-2,4-dien-1-al (4.5 g, 18 mmol) with triethyl 2-phosphoropropionate gave 3 g of ethyl 2,5-dimethyl-7-(4-methoxy- 2,3,6-trimethylphenyl)-hepta-2,4,6-trienoate as a yellow oil.

EXAMPLE 17

2,5-Dimethyl-7-(4-Methoxy-2,3,6-Trimethylphenyl)-Hepta-2,4,6-Trienoic Acid

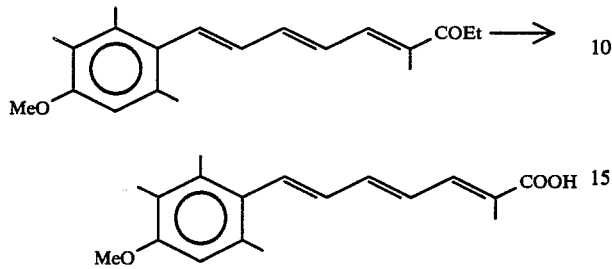

In a manner similar to Example 6, alkaline hydrolysis of ethyl 2,5-dimethyl-7-(4-methoxy-2,3,6-trimethylphenyl)-hepta-2,4,6-trienoate afforded, after trituration from ether, the corresponding acid as yellow powder, m.p. 188°–190° C.

Compounds of this invention are active against various skin disorders, such as acne and psoriasis, when tested according to models considered to be predictive of the clinical condition in humans. The models used were the rhino mouse procedure (Kligman, et al., J. Investigative Dermatology 73, 354 (1979)), the rabbit comedolytic procedure (Mills O. H., Kligman A. M.: Assay of Comedolytic Agents in the Rabbit Ear, Animal Models in Dermatology; Relevance to Human Dermatopharmacology and Dermatotoxicology, edited by H. I. Maibach, New York Churchill-Livingston, 1975, pp. 176-183) and the mouse epidermal cell culture procedure (Marcelo, et al., J. Cell Biol., 79, 356 (1978). Testing was done comparatively against standard retinoids known to be effective in these disorders and against a known α-methyl retinoid (2,7-dimethyl-9-(2,6,6-trimethyl-1-cyclohexene-1-yl)-2,3,6,8-nonatetraenoic acid, referred to as DTCNA).

Activity equal to or greater than the standards and the known compound was shown by 2,5,9-trimethyl-11-(2,6,6-trimethyl-1-cyclohexene-1-yl)-2,4,6,8,10-undecapentaenoic acid (TTCUA). Thus in the rabbit ear model at a concentration of 0.05%, it was equal to trans retinoic acid (TRA) in ability to reduce comedone size. In the rhino mouse model at the same concentration, it was equal to TRA in ability to reduce significantly the size of utriculi (pseudocomedones) and the amount of horny impaction in the utriculi. The skin of these mice showed moderate epidermal hyperplasia and significantly less wrinkling than the untreated control animals.

In the mouse epidermal cell culture at a concentration of 12 ug/ml, it reduced cell proliferation, as measured by inhibition of the uptake of tritrated thymidine into DNA. Table I shows percentage uptake relative to vehicle control (100%).

TABLE 1

| Day of Culture Exposure to Drug | TRA | CRA | TTCUA | DTCNA |
|---|---|---|---|---|
| 3 | 77 | 47 | 31 | 53 |
| 5 | 53 | 75 | 15 | 61 |
| 10 | 36 | 64 | 21 | 60 |

Percentage uptake with TTCUA is seen to be up to five fold less at all time points in comparison to both standards. Known compound DTCNA in contrast is seen to give about the same percentage uptake as the standard drugs at all three time points. Likewise TTCUA showed high anti-differentiation activity at 12 ug/ml in the mouse epidermal cell culture, as shown in Table II.

TABLE II

| Day of Culture Exposure to Drug | Vehicle Control | TRA | CRA | TTCUA | DTCNA |
|---|---|---|---|---|---|
| 3 | 3/6 | 3/5 | 2/7 | 2/6 | 3/6 |
| 6 | 3/5 | 3/5 | 2/7 | 0.5/8.5 | 2/6 |
| 10 | 7.5/2 | 2/6 | 2/6.5 | 1/7.5 | 2/5 |

The ratios in the table represent scoring of two measured parameters, culture staining by the Kreyberg technique (maximum differentiation 10) and nuclei enumeration (maximum differentiation 0). Thus the highest possible anti-differentiative activity would be given by the ratio 0/10. TTCUA is seen to be more active in both parameters than the two standards whereas the known compound is about the same as the standards.

Compounds of the present invention were found to have potent activity in regulating the formation of lipoxygenase and as such possess therapeutic value in the treatment of inflammatory conditions and allergic responses such as anaphylaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicostetraenoic acids (HETEs). Lipoxygenases are classified according to the position in the arachidonic acid which is oxygenated. Platelets metabolize arachidonic acid to 12-HETE, while polymorphonuclear leukocytes contain 5 and 15 lipoxygenases. It is known that 12-HETE and 5,12-diHETE are chemotactic for human neutrophils and eosinophils, and may augment the inflammation process. 5-HPETE is known to be a precursor of slow-reacting substance of anaphylaxis (SRS-A). The SRS family of molecules, such leukotrienes B, C, and D, have been shown to be potent bronchoconstrictors (see, NATURE 288, 484–486 (1980)).

The following protocol describes an assay to detect inhibitors of the lipoxygenase pathway. Such inhibitors are believed to be capable of modulating the biosynthesis of the leukotrienes, a property believed to be useful in treating asthma and inflammatory disease states.

PROTOCOL

A homogenate of human neutrophils containing lipoxygense activity is incubated for 5 minutes at 37° with $^{14}C$-arachidonic acid (AA). Citric Acid (2M) is used to quench the reaction. Following the addition of a trace amount of $^{3}H$-AA together with an excess of unlabeled AA to each tube, the mixture is extracted with chlorform/methanol. The organic layer is washed with dilute acid and an aliquot is transferred to glass tubes and dried. The residue is dissolved in a small volume of chloroform and an aliquot is spotted on silica gel TLC sheets. The sheets are developed with an ethyl acetate/isooctane/water/acetic acid solvent system. The AA-spots are identified with iodine vapors, cut out and placed in scintillation vials for counting. After adjusting for the extraction efficiency, the amount (pmole)

of $^{14}C$-AA in each of the tubes is quantitated. The pmoles of oxidized AA are obtained by subtracting the pmoles of AA remaining in the tubes containing active enzyme (control) from the pmoles of AA in the tubes acidified prior to the addition of enzyme (blank). The ability of the test compounds to modulate the activity of this enzyme is determined by an increase or decrease in the net amount of AA oxidized.

Table III shows the concentration required for inhibition of the 5-Lipoxygenese pathway (5-Lox/$I_{50}$ μm) for representative compounds of the present invention.

TABLE III

| Compound of Example | LOX, Rat PMN ($I_{50}$ μm) |
|---|---|
| 3B | 13 |
| 6 | 2 |
| 8 | 10 |
| TRA (Standard) | 90 |

The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk, sugar, certain types of clay and so forth. They may be administered orally in the form of solutions which may contain coloring and flavoring agents or they may be injected parenterally, that is intramuscularly, intravenously or subcutaneously. For parenteral administration, they may be used in the form of a sterile solution containing other solutes, for example, enough saline or glucose to make the solution isotonic. When applied topically for treating skin disorders, the present new products can be provided in the form of dusting powders, aerosol sprays, ointments, aqueous compositions including solutions and suspensions, cream lotions and the like. In this regard, any of the commonly employed extending agents can be used depending on the nature of the product as is well-known in the art.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally.

A convenient form for administration of the present new compounds are salts of those compounds in which $R_3$ is OH, particularly salts with alkali metals such as sodium and potassium, the ammonium salt and salts with organic amines, particularly those commonly employed in pharmaceutical formulations. The salts, of course, should be pharmaceutically-acceptable, that is the salt formation does not appreciably increase the toxicity of the therapeutic agent nor cause a toxic reaction in the host.

What is claimed is:

1. A therapeutic composition for the treatment of inflammatory conditions and allergic responses in a human host, in combination with at least one pharmaceutically-acceptable extender, a therapeutically effective amount of a compound of the general formula

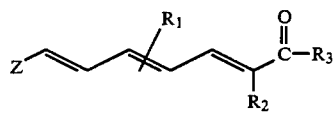

or a pharmaceutically acceptable salt thereof in which
$R_1$ is hydrogen or an alkyl group of from 1 to 5 carbon atoms;
$R_2$ is hydrogen or an alkyl group of from 1 to 5 carbon atoms;
$R_3$ is hydroxyl, alkoxy of from 1 to 5 carbon atoms, $NH_2$, $NHR_2$ or $HR_2R_2$; and
Z is a cycloalkyl, cycloalkenyl or cycloalkdienyl group substituted with from 0 to 5 alkyl groups, a keto group or a hydroxyl group or a phenyl group substituted with from 0 to 4 hydroxy, alkoxy, alkyl or trifluoromethyl groups or halogen atoms or combinations thereof, wherein said pharmaceutically-acceptable extender is in the form of tablets, capsules or solutions for oral administration; solutions for parenteral administration; dusting powders, aerosol sprays, ointments, creams and lotions for topical administration.

2. A method for treating inflammatory conditions and allergic responses in a human host which comprises administering to said host a therapeutically effective amount of at least one polyolefinic compound of the general formula

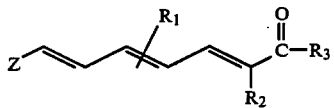

in which
$R_1$ is hydrogen or an alkyl group of from 1 to 5 carbon atoms;
$R_2$ is hydrogen or an alkyl group of from 1 to 5 carbon atoms;
$R_3$ is hydroxyl, alkoxy of from 1 to 5 carbon atoms, $NH_2$, $NHR_2$ or $NR_2R_2$;
and Z is a cycloalkyl, cycloalkenyl or cycloalkdienyl group substituted with from 0 to 5 alkyl groups, a keto group or a hydroxyl group or a phenyl group substituted with from 0 to 4 hydroxy, alkoxy, alkyl, or trifluoromethyl groups or halogen atoms or combinations thereof and the pharmaceutically-acceptable salts thereof.

* * * * *